United States Patent
Honda et al.

(10) Patent No.: US 10,290,843 B2
(45) Date of Patent: May 14, 2019

(54) BATTERY ASSEMBLY FOR MEDICAL INSTRUMENT AND MEDICAL INSTRUMENT UNIT

(71) Applicant: OLYMPUS CORPORATION, Hachioji-shi, Tokyo (JP)

(72) Inventors: Yoshitaka Honda, Hachioji (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/666,766

(22) Filed: Aug. 2, 2017

(65) Prior Publication Data
US 2017/0331084 A1 Nov. 16, 2017

Related U.S. Application Data

(63) Continuation of application No. PCT/JP2016/063768, filed on May 9, 2016.

(30) Foreign Application Priority Data

May 12, 2015 (JP) ................................. 2015-097393

(51) Int. Cl.
*H01M 2/10* (2006.01)
*A61B 17/00* (2006.01)
(Continued)

(52) U.S. Cl.
CPC ....... *H01M 2/1066* (2013.01); *A61B 1/00032* (2013.01); *A61B 17/00* (2013.01);
(Continued)

(58) Field of Classification Search
CPC ............ H01M 2/1066; H01M 10/0562; A61B 1/00032; A61B 1/00034
(Continued)

(56) References Cited

U.S. PATENT DOCUMENTS

2008/0057390 A1 3/2008 Kondo et al.
2010/0163325 A1 7/2010 Nakamura
(Continued)

FOREIGN PATENT DOCUMENTS

JP   H09-035724 A    2/1997
JP   2000-271143 A   10/2000
(Continued)

OTHER PUBLICATIONS

Jan. 24, 2017 Office Action issued in Japanese Patent Application No. 2016-567278.
(Continued)

*Primary Examiner* — James M Erwin
(74) *Attorney, Agent, or Firm* — Oliff PLC

(57) ABSTRACT

A battery assembly for a medical instrument that an operator can grip by a hand and operate, includes: a battery including a first laminated body unit including a solid electrolyte layer and configured to generate electrical energy; a casing including a wall section configured to store the battery inside; and a support provided in the casing and configured to support the battery apart from the wall section in a lamination direction of the first laminated body unit.

15 Claims, 7 Drawing Sheets

(51) Int. Cl.
*A61B 18/10* (2006.01)
*H01M 10/0562* (2010.01)
*H01M 10/0585* (2010.01)
*A61B 1/00* (2006.01)
*A61B 18/12* (2006.01)
*A61B 17/32* (2006.01)
*H01M 10/05* (2010.01)

(52) U.S. Cl.
CPC ...... *A61B 17/320068* (2013.01); *A61B 18/10* (2013.01); *A61B 18/12* (2013.01); *H01M 10/05* (2013.01); *H01M 10/0562* (2013.01); *H01M 10/0585* (2013.01); *A61B 2017/00734* (2013.01); *A61B 2018/1226* (2013.01); *H01M 2220/30* (2013.01)

(58) Field of Classification Search
USPC .......................................................... 429/96
See application file for complete search history.

(56) References Cited

U.S. PATENT DOCUMENTS

| | | | |
|---|---|---|---|
| 2013/0190759 A1 | 7/2013 | Waaler et al. | |
| 2013/0280598 A1 | 10/2013 | Shigematsu et al. | |
| 2013/0345504 A1* | 12/2013 | Shamir | A61B 1/041 600/104 |
| 2014/0023922 A1* | 1/2014 | Isshiki | H01G 11/22 429/211 |
| 2014/0207124 A1 | 7/2014 | Aldridge et al. | |
| 2014/0370364 A1 | 12/2014 | Kim et al. | |
| 2015/0044559 A1* | 2/2015 | Toyoda | H01M 4/13 429/217 |

FOREIGN PATENT DOCUMENTS

| | | |
|---|---|---|
| JP | 2004-139775 A | 5/2004 |
| JP | 2008-084851 A | 4/2008 |
| JP | 2010-118159 A | 5/2010 |
| JP | 2013-126430 A | 6/2013 |
| JP | 2013-150803 A | 8/2013 |
| JP | 2013-229257 A | 11/2013 |
| JP | 2015-111532 A | 6/2015 |

OTHER PUBLICATIONS

Jul. 5, 2016 International Search Report issued in Patent Application No. PCT/JP2016/063768.
Nov. 23, 2017 International Preliminary Report on Patentability issued in International Patent Application No. PCT/JP2016/063768.
Dec. 13, 2018 Search Report issued in European Patent Application No. 16792663.3.

* cited by examiner

BATTERY ASSEMBLY FOR MEDICAL INSTRUMENT AND MEDICAL INSTRUMENT UNIT

CROSS-REFERENCE TO RELATED APPLICATIONS

This application is a Continuation Application of PCT Application No. PCT/JP2016/063768, filed May 9, 2016 and based upon and claiming the benefit of priority from prior Japanese Patent Application No. 2015-097393, filed May 12, 2015, the entire contents of all of which are incorporated herein by reference.

BACKGROUND OF THE INVENTION

1. Field of the Invention

The present invention relates to a battery assembly for a medical instrument and a medical instrument unit using an all-solid-state battery.

2. Description of the Related Art

There is known a so-called all-solid-state battery whose electrolyte is not a liquid but a solid, as disclosed in, for example, Jpn. Pat. Appln. KOKAI Publication No. 2010-118159.

BRIEF SUMMARY OF THE INVENTION

According to one aspect of the present invention, there is provide a battery assembly for a medical instrument that an operator can grip by a hand and operate, includes: a battery including a first laminated body unit including a positive electrode layer, a solid electrolyte layer, and a negative electrode layer laminated sequentially to define a lamination direction and configured to generate electrical energy; a casing including a wall section configured to store the battery inside; and a support provided in the casing and configured to support the battery apart from the wall section in the lamination direction.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will now be described with reference to the accompanying drawings.

The first embodiment will be described with reference to FIG. 1 to FIG. 3C.

Figure 1:
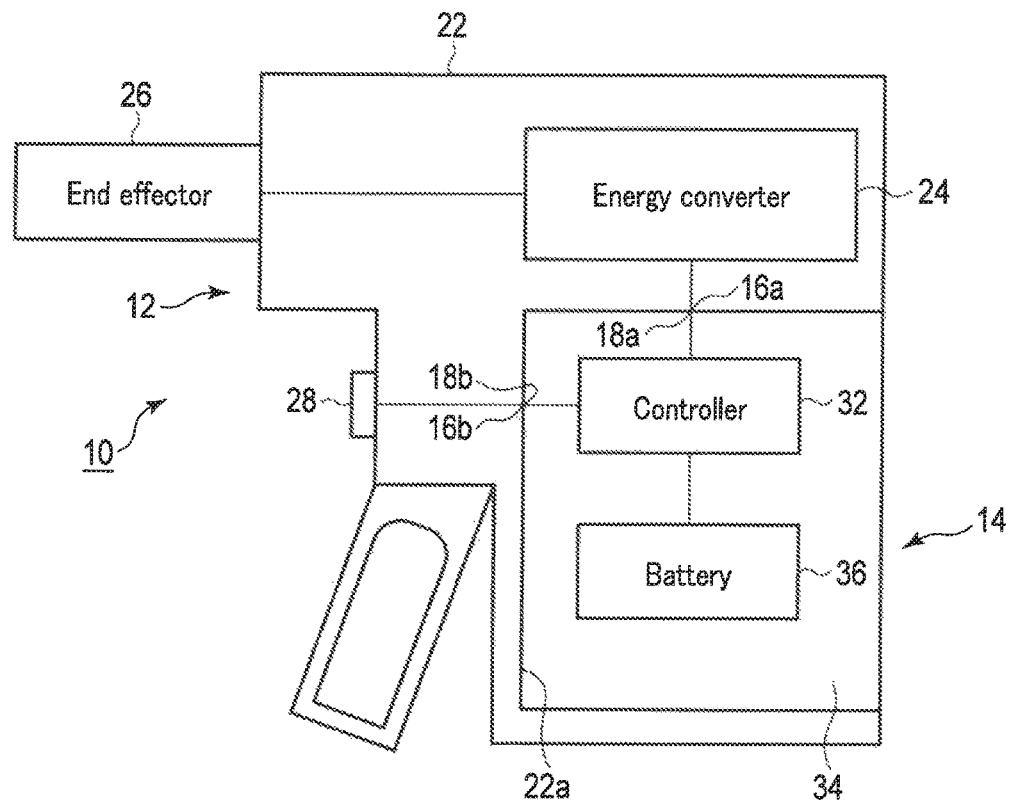
FIG. 1 is a schematic view showing a medical instrument unit according to a first embodiment.

As shown in FIG. 1, a medical instrument unit 10 includes a medical instrument main body 12 and a battery assembly 14 for a medical instrument. Note that the battery assembly 14 is used for the appropriate medical instrument main body 12 that performs a treatment by converting electrical energy into appropriate energy, for example, a cordless ultrasonic treatment instrument, a high-frequency treatment instrument, or an endoscope. The medical instrument main body 12 is not limited to a cordless instrument and may use the battery assembly 14 as a backup power supply.

The medical instrument main body 12 according to this embodiment includes a medical instrument housing 22, an energy converter 24 provided in the housing 22, and an end effector 26 provided on the housing 22. The energy converter 24 may be fixed to the housing 22 or is preferably detachable from the housing 22. An operator can grip the housing 22 by, for example, one hand such as the right hand and operate it. For example, when the operator operates a switch 28 provided on the housing 22 by the hand gripping the housing 22, the energy converter 24 converts electrical energy generated by the battery assembly 14 into appropriate energy. The energy converted by the energy converter 24 is transmitted to the end effector 26, and the end effector 26 performs an appropriate treatment. Note that the switch 28 is electrically connected to a controller 32 (to be described later) in a state in which the battery assembly 14 is attached to the medical instrument main body 12.

For example, a slot 22a is formed in the housing 22 of the medical instrument main body 12. The battery assembly 14 is, for example, disposed in the slot 22a of the housing 22 and fixed or supported. A casing 34 (to be described later) of the battery assembly 14 is preferably integrated with the medical instrument housing 22. That is, the battery assembly 14 is preferably detachable from the medical instrument main body 12 or is also preferably formed to be undetachable from the medical instrument main body 12.

As shown in FIG. 1 to FIG. 3C, the battery assembly 14 includes the controller 32, the casing 34, a battery 36 incorporating a first laminated body unit 36a (see FIG. 2) of an all-solid-state battery arranged in the casing 34, and supporters 38 (see FIG. 3A to FIG. 3C) that support the battery 36 in the casing 34. The casing 34 is made of, for example, a metal material or a plastic material. In the form shown in FIG. 1, the battery assembly 14 includes the controller 32. However, the medical instrument main body 12 may include the controller 32. In FIG. 1, the controller 32 is disposed in the battery assembly 14. However, the controller 32 is also preferably disposed in the medical instrument main body 12.

To the energy converter 24 in the medical instrument main body 12, power is supplied from the battery assembly 14 by appropriate electrical connection (for example, contact power supply between contacts 16a and 18a). If the battery assembly 14 is not detachable from the medical instrument main body 12 but fixed, the energy converter 24 of the medical instrument main body 12 and the battery assembly 14 are always electrically connected.

To the energy converter 24 of the medical instrument main body 12, power is also preferably supplied from the battery assembly 14 by non-contact power supply. When performing non-contact power supply, each of the medical instrument main body 12 and the battery assembly 14 includes a known coil (not shown) that transmits/receives power. As a method of the non-contact power supply, a known electromagnetic resonance method or electromagnetic induction method can appropriately be selected and used.

Note that the controller 32 includes a processor including a CPU or ASIC.

As shown in FIG. 1, contacts 16a and 16b (not illustrated in FIG. 3A to FIG. 3C) of the controller 32 of the battery assembly 14 are electrically connected to contacts 18a and 18b of the medical instrument main body 12, respectively. More specifically, when the battery assembly 14 is attached to the slot 22a of the medical instrument main body 12, the energy converter 24 and the controller 32 are electrically connected by the contact between the contacts 16a and 18a. Similarly, the switch 28 and the controller 32 are electrically connected by the contact between the contacts 16b and 18b. For this reason, for example, when the operator operates the switch 28 and inputs a signal to the controller 32, the controller 32 transmits appropriate energy converted by the energy converter 24 to the end effector 26.

At the time of charging, for example, the controller 32 optimizes charging of the battery 36 of the battery assembly 14. When supplying electrical energy, the controller 32 appropriately controls the electrical energy (power) to be supplied to the end effector 26.

Figure 2:
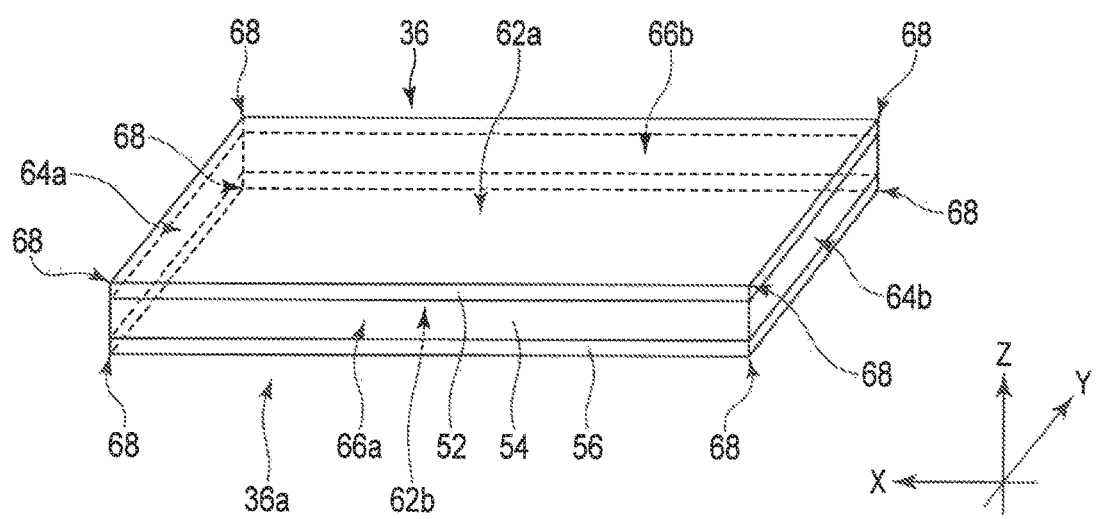
FIG. 2 is a schematic perspective view showing the structure of the battery of the battery assembly of the medical instrument unit according to the first embodiment.

Types of the first laminated body unit 36a used as the all-solid-state battery in the battery 36 shown in FIG. 2 include, for example, a bulk type and a thin film type. The first laminated body unit 36a of the battery 36 supported in the casing 34 can be either of the bulk type and the thin film type of all-solid-state batteries. The first laminated body unit 36a of the bulk type will be exemplified here.

As shown in FIG. 2, the first laminated body unit 36a of the battery 36 includes a positive electrode layer 52, a solid electrolyte layer 54, and a negative electrode layer 56. Each of the positive electrode layer 52 and the negative electrode layer 56 includes a current collector (not shown). In the first laminated body unit 36a, the positive electrode layer 52, the solid electrolyte layer 54, and the negative electrode layer 56 are sequentially laminated to define a lamination direction Z. The thickness of the positive electrode layer 52, the solid electrolyte layer 54, and the negative electrode layer 56 in the lamination direction Z is appropriately set. In the state in which the first laminated body unit 36a is thus formed, the battery 36 generates electrical energy.

As the positive electrode layer 52, the solid electrolyte layer 54, and the negative electrode layer 56 of the first laminated body unit 36a of the battery 36, arbitrary substances employable in the all-solid-state battery can be used. As the positive electrode layer 52, for example, an oxide active material or a sulfide active material is usable. As the solid electrolyte layer 54, for example, an inorganic sold electrolyte substance such as a sulfide sold electrolyte material, an oxide sold electrolyte material, or a nitride sold electrolyte material is usable. For this reason, the electrolyte of the solid electrolyte layer 54 is not a liquid but a solid. As the negative electrode layer 56, a material capable of occluding and emitting metal ions can be used. For example, a carbon active material or a metal active material is usable.

The battery 36 is formed into, for example, an almost rectangular parallelepiped shape as a whole. The battery 36 includes a pair of first surfaces 62 (62a and 62b) having the largest surface area, and a pair of second surfaces 64 (64a and 64b) and a pair of third surfaces 66 (66a and 66b) having surface areas smaller than that of the first surfaces 62a and 62b. One first surface 62a is the surface of the positive electrode layer 52 including a current collector, and the other first surface 62b is the surface of the negative electrode layer 56 including a current collector. The second surfaces 64a and 64b and the third surfaces 66a and 66b are formed by the edge portions of the positive electrode layer 52, the solid electrolyte layer 54, and the negative electrode layer 56. Note that when an XYZ orthogonal coordinate system with axes orthogonal to each other is employed, preferably, the first surfaces 62a and 62b are defined as an XY plane and a plane parallel to it, the second surfaces 64a and 64b are defined as an YZ plane and a plane parallel to it, and the third surfaces 66a and 66b are defined as a ZX plane and a plane parallel to it. Note that the first surfaces 62a and 62b, the second surfaces 64a and 64b, or the third surfaces 66a and 66b are preferably parallel to each other. However, they need not always be parallel. Additionally, in FIG. 2, the second surfaces 64a and 64b and the third surfaces 66a and 66b have different areas. However, the second surfaces 64a and 64b and the third surfaces 66a and 66b also preferably have almost the same area.

The battery 36 includes eight corners 68 each formed by three surfaces. The eight corners 68 each formed by three surfaces need not always have the surfaces intersecting at right angles and are also preferably formed as curved surfaces, as a matter of course.

Since the battery 36 has a thin plate shape, the solid electrolyte layer 54 of the first laminated body unit 36a is broken (cracked) readily not by an impact loaded to one of the second and third surfaces (end faces) 64a, 64b, 66a, and 66b but by an impact loaded to one of the first surfaces 62a and 62b, as can easily be understood by so-called those skilled in the art, although it depends on the strength of the impact. In particular, the solid electrolyte layer 54 is broken most readily when an impact is loaded to the vicinity of the center of one of the first surfaces 62a and 62b, as can easily be understood by so-called those skilled in the art.

Figure 3A:
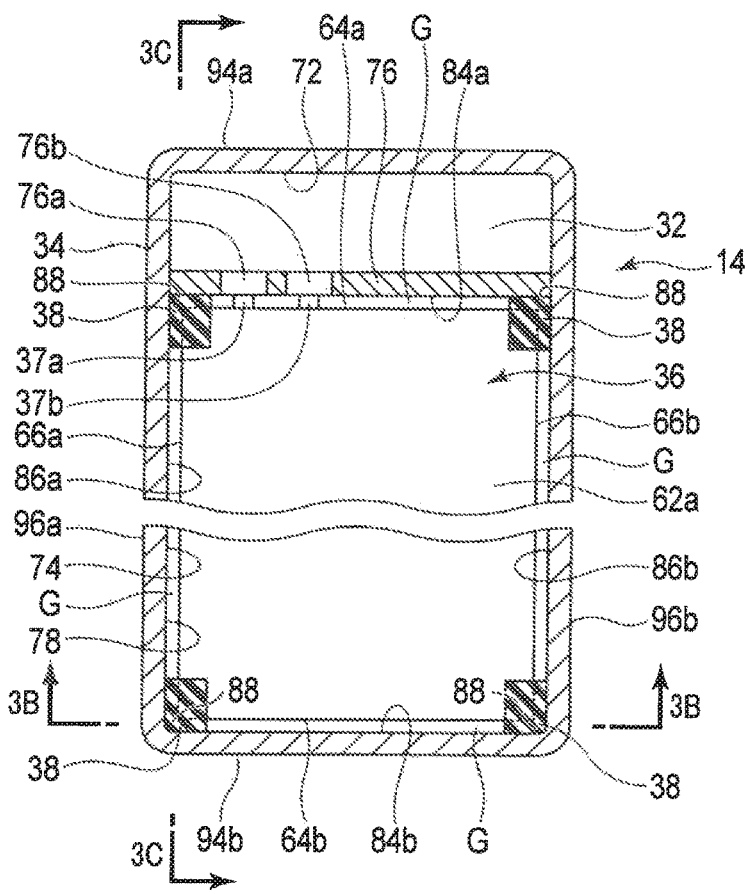
FIG. 3A is a schematic longitudinal sectional view of the battery assembly of the medical instrument unit according to the first embodiment taken along a line 3A-3A in FIG. 3C.
Figure 3B:
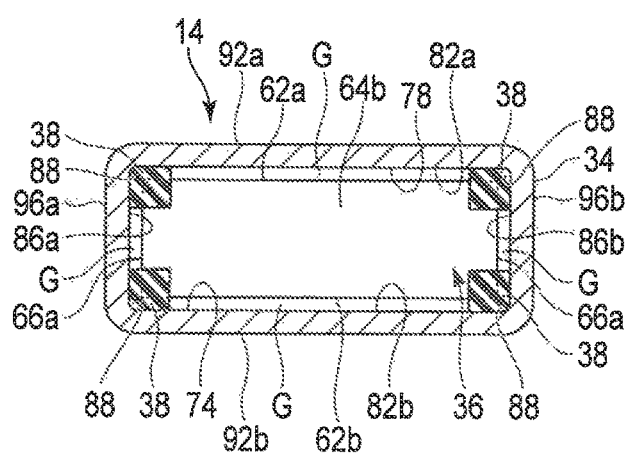
FIG. 3B is a schematic sectional view of the battery assembly of the medical instrument unit according to the first embodiment taken along a line 3B-3B in FIG. 3A.
Figure 3C:
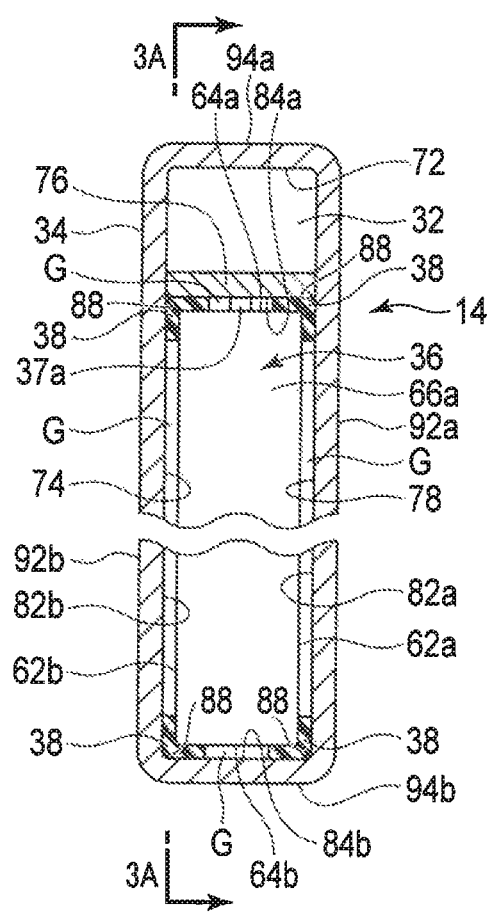
FIG. 3C is a schematic longitudinal sectional view of the battery assembly of the medical instrument unit according to the first embodiment taken along a line 3C-3C in FIG. 3A.

As shown in FIG. 3A to FIG. 3C, the casing 34 that stores the battery 36 is formed into, for example, a box shape, and more specifically, formed into an almost rectangular parallelepiped shape. The casing 34 has an internal space larger than the battery 36 where the battery 36 is stored. The casing 34 includes a first storage portion 72 in which the controller 32 is stored, a second storage portion 74 in which the battery 36 is stored, and a partition 76 that separates the first storage portion 72 and the second storage portion 74 from each other. The partition 76 includes terminals 76a and 76b that electrically connect contacts 37a and 37b of the battery 36 to the controller 32.

The second storage portion 74 of the casing 34 includes a wall section 78 configured to store the battery 36 inside. The wall section 78 includes first inner surfaces 82 (82a and 82b) that face each other and also face the pair of first surfaces 62 in a state in which the battery 36 is stored in the second storage portion 74, second inner surfaces 84 (84a and 84b) that face each other and face the pair of second surfaces 64, and third inner surfaces 86 (86a and 86b) that face each other and face the pair of third surfaces 66. Note that the casing 34 includes first outer surfaces 92a and 92b on the back sides of the first inner surfaces 82a and 82b, a second outer surface 94b on the back side of the second inner surface 84b, and third outer surfaces 96a and 96b on the back sides of the third inner surfaces 86a and 86b. Note that a position 94a in FIG. 3A and FIG. 3C corresponds to the second outer surface. The above-described contacts 18a and 18b (see FIG. 1) of the battery 36 are disposed on the second outer surface 94a.

The supporters 38 that support the battery 36 are disposed in the second storage portion 74 of the casing 34. The supporters 38 are preferably made of, for example, an elastic material including a resin material such as a rubber material and so on capable of flexibly bending, a porous material such as foamed styrol and so on, or a gel material and so on having shock absorbency, or an elastic material such as a coil spring (not shown), a rubber material and so on that appropriately adjusts the distance from the wall section 78 of the casing 34 by elastic deformation. Note that the supporters 38 preferably have electrical insulating properties. In addition, the supporters 38 preferably have a proper heat resistance.

In this embodiment, the supporters 38 are fixed to or supported by eight corners 88 of the wall section 78. The supporters 38 need not always be arranged at all the eight corners 88. One supporter 38 may suffice if the supporter 38 can support the battery 36. That is, the supporters 38 need only support one of the eight corners 68 of the battery 36.

Here, the supporters 38 are each assumed to support the three surfaces of a corresponding one of the eight corners 68 of the battery 36. One of the eight supporters 38 supports, for example, the first surface 62a, the second surface 64b, and the third surface 66b at the upper right corner in FIG. 2.

The supporters 38 support the battery 36 apart from the wall section (inner surface) 78 of the casing 34. Hence, a gap (space) G is formed between the wall section 78 of the casing 34 and the outer surface of the battery 36. For this reason, in a state in which the battery 36 is stored in the second storage portion 74 of the casing 34, one first surface 62a of the battery 36 is located at a position close to one first inner surface 82a but faces the first inner surface 82a while being spaced apart by the appropriate gap G, and the other first inner surface 82b faces the other first surface 62b of the battery 36 closely while being spaced apart by the appropriate gap G. In addition, one second inner surface 84a faces one second surface 64a of the battery 36 closely while being spaced apart by the appropriate gap G, and the other second inner surface 84b faces the other second surface 64b of the battery 36 closely while being spaced apart by the appropriate gap G. One third inner surface 86a faces one third surface 66a of the battery 36 closely while being spaced apart by the appropriate gap G, and the other third inner surface 86b faces the other third surface 66b of the battery 36 closely while being spaced apart by the appropriate gap G.

Each supporter 38 is preferably formed as small as possible and supports a corresponding corner 68 of the battery 36 at three points in an almost floating state. In this case, for example, the supporter 38 at the upper right corner in FIG. 2 has a small contact area to the first surface 62a, the second surface 64b, and the third surface 66b.

If the battery assembly 14 is dropped, and an impact is loaded to the casing 34, the impact is transmitted from the casing 34 to the battery 36 via the supporters 38. At this time, the gap G is formed between the casing 34 and the battery 36. In addition, the contact area between the supporters 38 and the battery 36 is small, and the impact is hardly transmitted to the solid electrolyte layer 54.

The supporters 38 are made of, for example, an elastically deformable material, or support the battery 36 via an elastically deformable material. For this reason, the impact loaded to the battery assembly 14 is largely attenuated by the supporters 38. Hence, the impact loaded to the battery assembly 14 is not directly transmitted from the casing 34 to the battery 36 but transmitted in an attenuated state.

The supporters 38 preferably support the battery 36 at, for example, all the corners (eight corners) 68 in an almost floating state with an appropriate play. In this state, when the impact loaded to the casing 34 is transmitted to the battery 36 via the supporters 38, the supporters 38 buffer the impact loaded to the battery assembly 14 by the play in cooperation with the gap G. For this reason, when the impact loaded to the battery assembly 14 is transmitted to the battery 36 via the casing 34, the impact is transmitted in a largely attenuated state. That is, transmission of a large impact to the battery 36 is prevented or suppressed.

For example, when the battery assembly 14 is dropped on a worktable, an external force can be loaded to one of the pair of first outer surfaces 92a and 92b of the casing 34 by a projection or the like. When the impact is loaded to the first outer surface 92a, the impact is transmitted to the first inner surface 82a. Since the gap G is formed between the first inner surface 82a and the first surface 62a of the battery 36, the first inner surface 82a of the casing 34 is prevented from directly pressing the first surface 62a of the battery 36.

Similarly, even if an impact is loaded to the second outer surface 94a, the second inner surface 84a of the casing 34 is prevented from directly pressing the second surface 64a of the battery 36 because the gap G is formed between the second inner surface 84a and the second surface 64a of the battery 36. Additionally, even if an impact is loaded to the third outer surface 96a, the third inner surface 86a of the casing 34 is prevented from directly pressing the third surface 66a of the battery 36 because the gap G is formed between the third inner surface 86a and the third surface 66a of the battery 36.

As shown in FIG. 1, the battery assembly 14 is attached to the housing 22 of the medical instrument main body 12 and forms the medical instrument unit 10. Even if the medical instrument unit 10 is dropped on, for example, a worktable (not shown), when the impact loaded to the housing 22 is transmitted via the casing 34 and the supporters 38, the supporters 38 buffer the impact loaded to the casing 34 in cooperation with the gap G. For this reason, when the impact loaded to the casing 34 is transmitted to the battery 36, it is transmitted in a largely attenuated state. That is, transmission of a large impact to the battery 36 is prevented or suppressed.

As described above, according to this embodiment, the followings are possible.

The battery 36 including the first laminated body unit 36a is supported in the casing 34 by the supporters 38 made of an elastically deformable material or including an elastically deformable material. The gap G is formed between the battery 36 and the wall section 78 of the casing 34. For this reason, an impact loaded to the battery assembly 14 can be prevented from being transmitted from the casing 34 to the battery 36 via the supporters 38. Hence, the battery assembly 14 according to this embodiment can prevent damage to the battery 36 including the solid electrolyte layer 54 as much as possible when, for example, the battery assembly 14 is dropped on a worktable, and an impact is loaded.

In particular, the gap G exists between the first surfaces 62a and 62b of the battery 36 and the first inner surfaces 82a and 82b of the wall section 78 of the casing 34. For this reason, an impact loaded to the first outer surfaces 92a and 92b of the casing 34 can be prevented from being transmitted to one of the first surfaces 62a and 62b.

It is therefore possible to provide the battery assembly 14 for a medical instrument and the medical instrument unit 10 capable of suppressing transmission of an impact to the first laminated body unit (all-solid-state battery) 36a and occurrence of damage such as a crack even if an impact is applied to the casing 34.

Note that the first laminated body unit 36a itself also has appropriate shock resistance. Even if an impact is applied to the casing 34, and the impact is transmitted to the first laminated body unit (all-solid-state battery) 36a, the shock resistance can prevent damage to the first laminated body unit 36a.

The second embodiment will be described next with reference to FIG. 4A to FIG. 4C. This embodiment is a modification the first embodiment. The same reference numerals as in the first embodiment are added to the same members as much as possible, and a detailed description thereof will be omitted.

Figure 4A:
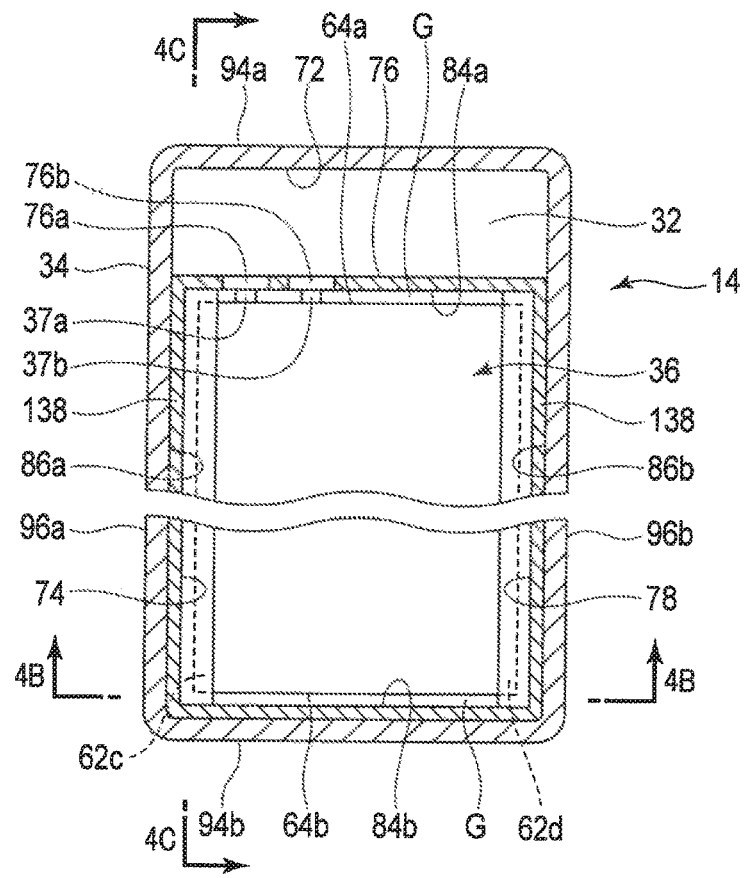
FIG. 4A is a schematic longitudinal sectional view of the battery assembly of a medical instrument unit according to a second embodiment taken along a line 4A-4A in FIG. 4C.
Figure 4B:
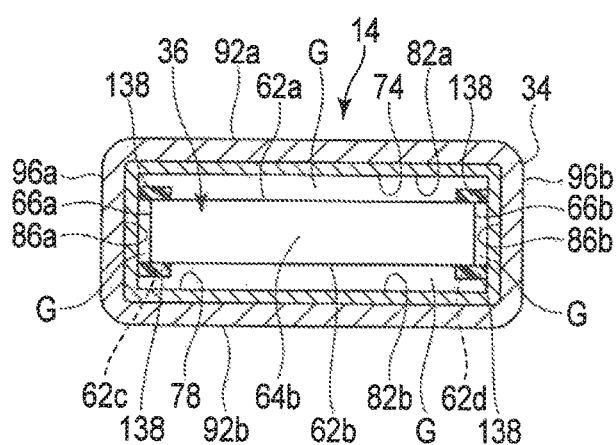
FIG. 4B is a schematic sectional view of the battery assembly of the medical instrument unit according to the second embodiment taken along a line 4B-4B in FIG. 4A.
Figure 4C:
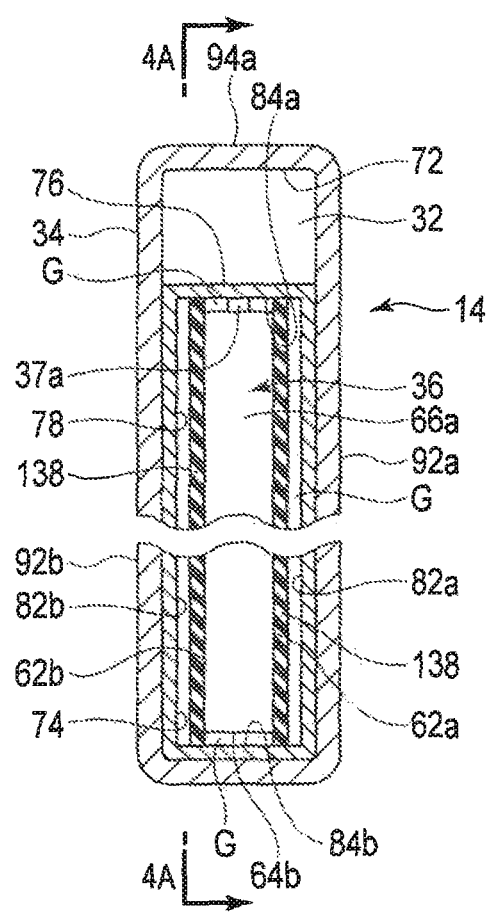
FIG. 4C is a schematic longitudinal sectional view of the battery assembly of the medical instrument unit according to the second embodiment taken along a line 4C-4C in FIG. 4A.

As shown in FIG. 4A to FIG. 4C, supporters 138 according to this embodiment almost wholly support, for example, edge portions 62c and 62d in first surfaces 62a and 62b close to third surfaces 66a and 66b. That is, in this modification, the supporters 138 support the vicinities of the ends of the first surfaces 62a and 62b (the vicinities of second surfaces 64a and 64b). Note that, like the above-described supporters 38, the supporters 138 are preferably made of an elastic material including a resin material such as a rubber material and so on capable of flexibly bending, or a gel material and so on, or an elastic material such as a coil spring (not shown), a rubber material and so on that appropriately adjusts the distance from a wall section 78 of a casing 34 by elastic deformation. In addition, gaps G are formed between the supporters 138 and first inner surfaces 82a and 82b of the wall section 78 of the casing 34 such that when an external force is applied to the wall section 78, and the first inner surfaces 82a and 82b are deformed, the first inner surfaces 82a and 82b do not directly contact the supporters 138.

The gaps G are formed between the first inner surfaces 82a and 82b of the wall section 78 and the first surfaces 62a and 62b of a battery 36. When an impact is loaded to a battery assembly 14, the impact is transmitted from the casing 34 to the battery 36 via the supporters 138. At this time, since the gaps G are formed between the first inner surfaces 82a and 82b of the wall section 78 of the casing 34 and the first surfaces 62a and 62b of the battery 36, the impact is hardly transmitted to the first surfaces 62a and 62b.

When an impact is loaded to the first outer surface 92a, the impact is transmitted to the first inner surface 82a. Since the gap G is formed between the first inner surface 82a and the first surface 62a of the battery 36, the first inner surface 82a of the casing 34 is prevented from directly pressing the first surface 62a of the battery 36.

The gaps G are formed between second inner surfaces 84a and 84b of the wall section 78 and the second surfaces 64a and 64b of the battery 36. For this reason, even if an impact is loaded to a second outer surface 94a, the second inner surface 84a of the casing 34 is prevented from directly pressing the second surface 64a of the battery 36. In addition, the gaps G are formed between third inner surfaces 86a and 86b of the wall section 78 and third surfaces 66a and 66b of the battery 36. For this reason, even if an impact is loaded to a third outer surface 96a, the third inner surface 86a of the casing 34 is prevented from directly pressing the third surface 66a of the battery 36.

The third embodiment will be described next with reference to FIG. 5. This embodiment is a modification the first and second embodiments. The same reference numerals as in the first and second embodiments are added to the same members as much as possible, and a detailed description thereof will be omitted.

Figure 5:
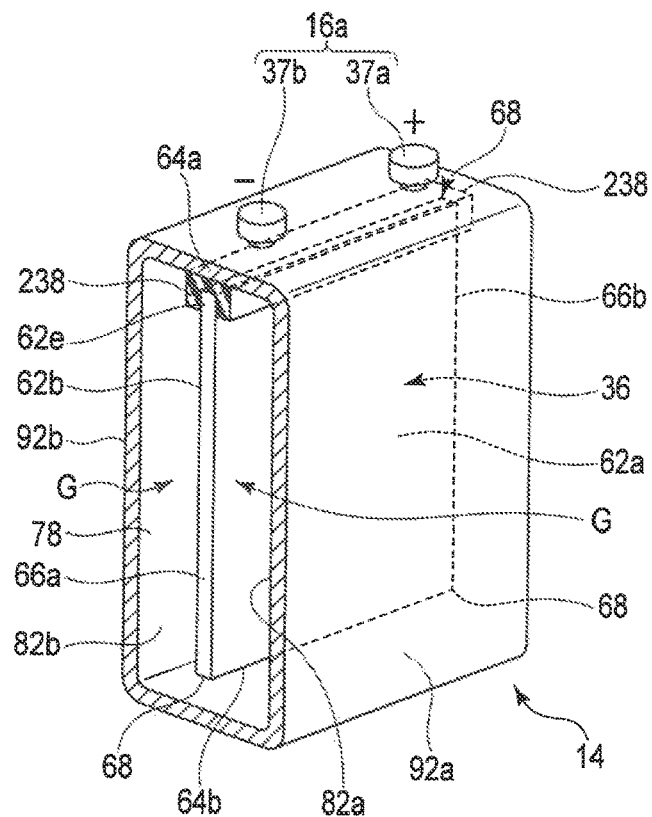
FIG. 5 is a schematic perspective view showing the battery assembly of a medical instrument unit according to a third embodiment.

As shown in FIG. 5, a supporter 238 according to this embodiment almost wholly supports, for example, an edge portion 62e of first surfaces 62a and 62b close to one of a pair of second surfaces 64a and 64b. The supporter 238 may support one corner 68 or may support the edge portion 62e at a plurality of points. In addition, gaps G are formed between the supporter 238 and first inner surfaces 82a and 82b of a wall section 78 of a casing 34 such that when an external force is applied to the wall section 78, and the first inner surfaces 82a and 82b are deformed, the first inner surfaces 82a and 82b do not directly contact the supporter 238.

The gaps G are formed between the first inner surfaces 82a and 82b of the wall section 78 and the first surfaces 62a and 62b. When an impact is loaded to a battery assembly 14, the impact is transmitted from the casing 34 to a battery 36 via the supporter 238. At this time, since the gap G is formed between the casing 34 and the battery 36, the impact is hardly transmitted to a solid electrolyte layer 54.

Note that in this embodiment as well, the gap G is preferably formed between the supporter 238 and the second surface 64a, like the gap G shown in FIG. 4B.

The fourth embodiment will be described next with reference to FIG. 6. This embodiment is a modification the first to third embodiments. The same reference numerals as in the first to third embodiments are added to the same members as much as possible, and a detailed description thereof will be omitted.

Figure 6:
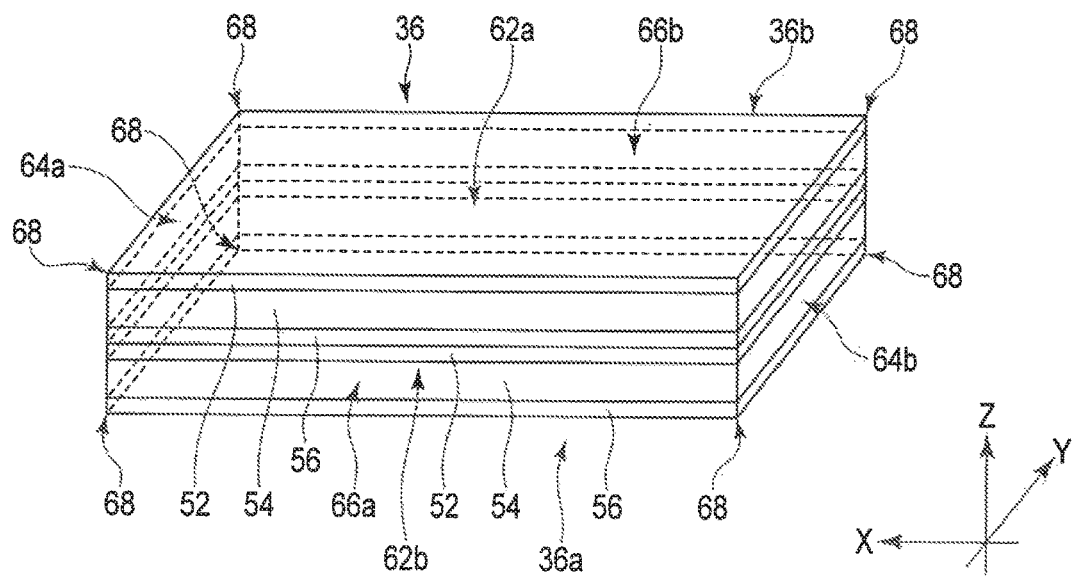
FIG. 6 is a schematic perspective view showing the structure of the battery of the battery assembly of a medical instrument unit according to a fourth embodiment.

As shown in FIG. 6, a battery 36 of a battery assembly 14 for a medical instrument includes a second laminated body unit 36b of an all-solid-state battery arranged in a casing 34 in addition to a first laminated body unit 36a.

In the second laminated body unit 36b, a positive electrode layer 52, a solid electrolyte layer 54, and a negative electrode layer 56 are sequentially laminated along a lamination direction Z, in addition to the first laminated body unit 36a.

A terminal (not shown) of the positive electrode layer 52 of the first laminated body unit 36a of the battery 36 according to this embodiment is connected to a terminal (not shown) of the negative electrode layer 56 of the second laminated body unit 36b adjacent to the first laminated body unit 36a. In the battery assembly 14 according to this embodiment, the plurality of laminated body units 36a and 36b may be connected in series or may be connected in parallel.

Supporters 38 of the casing 34 support the battery 36 including the first laminated body unit 36a and the second laminated body unit 36b. The supporters 38 support the battery 36 including the first laminated body unit 36a and the second laminated body unit 36b apart from a wall section 78 of the casing 34. That is, gaps G are formed between the first laminated body unit 36a and the wall section 78 of the casing 34 and between the second laminated body unit 36b and the wall section 78 of the casing 34. Hence, the supporters 38 support the battery 36 apart from the wall section 78 in the lamination direction Z.

Note that in addition to a case in which only the first laminated body unit 36a is provided and a case in which the first laminated body unit 36a and the second laminated body unit 36b are provided, the battery 36 also preferably further includes a laminated body unit, as a matter of course. That is, the battery 36 preferably includes only one laminated body unit 36a and also preferably includes a plurality of laminated body units 36a, 36b, . . . .

That is, in the first to third embodiments, the description has been made assuming that each of the positive electrode layer 52, the solid electrolyte layer 54, and the negative electrode layer 56 of the battery 36 includes one layer for the descriptive convenience. As shown in FIG. 6, a plurality of layers are preferably formed in the order of the positive electrode layer 52, the solid electrolyte layer 54, the negative electrode layer 56, the positive electrode layer 52, the solid electrolyte layer 54, and the negative electrode layer 56, as a matter of course. That is, a plurality of sets each including the positive electrode layer 52, the solid electrolyte layer 54, the negative electrode layer 56 are also preferably adjacently stored in one casing 34. That is, to increase the battery capacity, the battery 36 in the casing 34 preferably includes a plurality of laminated body units laminated. However, if an appropriate capacity can be ensured, one laminated body unit may suffice.

The fifth embodiment will be described next with reference to FIG. 7. This embodiment is a modification the first to fourth embodiments. The same reference numerals as in the first to fourth embodiments are added to the same members as much as possible, and a detailed description thereof will be omitted.

Figure 7:
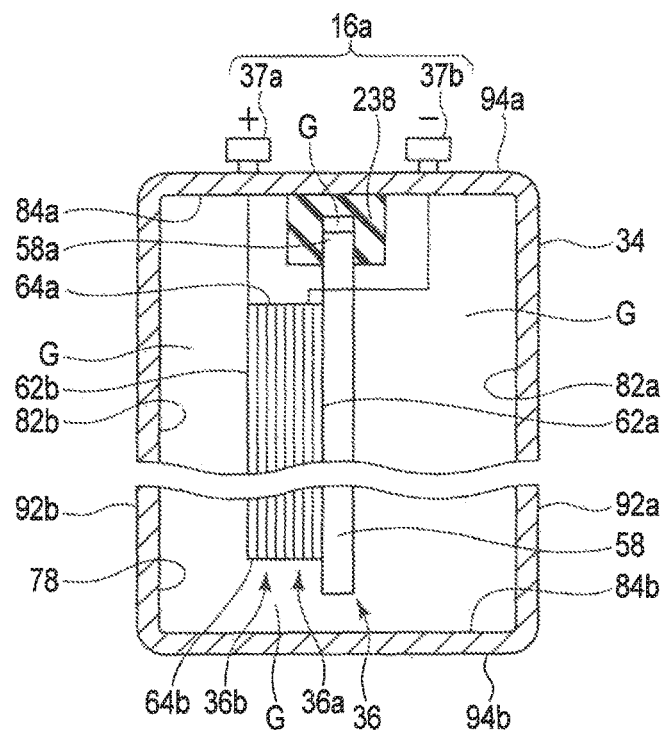
FIG. 7 is a schematic sectional view showing the battery assembly of a medical instrument unit according to a fifth embodiment.

As shown in FIG. 7, a thin film type battery is also preferably used as the all-solid-state battery of a battery 36. The battery 36 according to this embodiment includes a substrate 58. That is, the battery 36 includes the substrate 58 that supports at least one of a positive electrode layer 52 and a negative electrode layer 56. Here, a first laminated body unit 36a includes the substrate 58 in addition to the positive electrode layer 52, a solid electrolyte layer 54, and the negative electrode layer 56. Note that a second laminated body unit 36b includes the positive electrode layer 52, the solid electrolyte layer 54, and the negative electrode layer 56. That is, the substrate 58 is commonly used for the first laminated body unit 36a and the second laminated body unit 36b. The substrate 58 is preferably formed to have the function of a controller 32 described above. That is, as shown in FIG. 7, a battery assembly 14 does not always need the controller 32. This also applies to the other embodiments.

The laminated body unit 36a including the substrate 58 is also supported by at least one of supporters 38, 138, and 238, like the laminated body unit 36a of the battery 36 described in the first to fourth embodiments. An example in which the supporter 238 is used will be described here as a modification of the fourth embodiment. However, the supporters 38 or 138 can appropriately be used, as a matter of course.

Note that as shown in FIG. 7, the substrate 58 is preferably formed to be larger than a first surface 62a of the second laminated body unit 36b (the first surface 62a of the battery 36).

The supporter 238 supports an edge portion 58a of the substrate 58 apart from first inner surfaces 82a and 82b of a wall section 78 of a casing 34 in a lamination direction Z. At this time, gaps G are formed between the first surface 62a of the battery 36 and the first inner surface 82a, between second surfaces 64a and 64b and second inner surfaces 84a and 84b, and between third surfaces 66a and 66b and third inner surfaces 86a and 86b. For this reason, the gaps G prevent the solid electrolyte layer 54 of the battery 36 from being broken by an impact to the casing 34 as much as possible, as described in the first to fourth embodiments. In addition, the supporter 238 is provided apart from the first inner surfaces 82a and 82b of the wall section 78 of the casing 34 at the gap G such that when an external force is applied to the wall section 78, and the first inner surfaces 82a and 82b are deformed, the first inner surfaces 82a and 82b do not directly contact the supporters 238.

Figure 8:
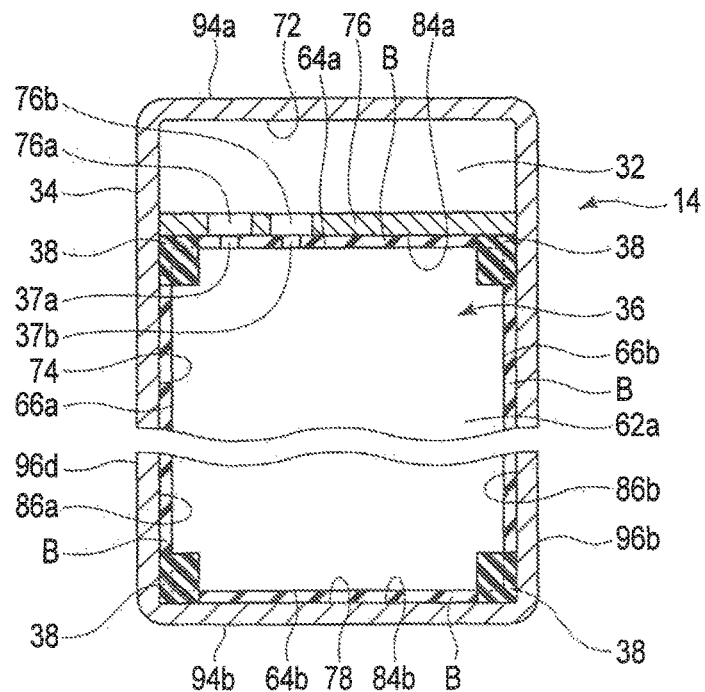
FIG. 8 is a schematic longitudinal sectional view of the battery assembly of a medical instrument unit according to a sixth embodiment.

The sixth embodiment will be described next with reference to FIG. 8. This embodiment is a modification the first to fifth embodiments. The same reference numerals as in the first to fifth embodiments are added to the same members as much as possible, and a detailed description thereof will be omitted. This embodiment will be described here as a modification of the first embodiment. However, in the second to fifth embodiments as well, a buffer B to be described later can appropriately be arranged in place of the gap G.

In this embodiment, the buffer B made of a gel substance or a porous material such as foamed styrol is arranged in place of the gap G described in the first to fifth embodiments. The buffer B need not always fill the entire gap G and may be arranged only partially. The buffer B preferably has electrical insulating properties. In addition, the buffer B preferably has a proper heat resistance.

When an impact is loaded to a casing 34, the buffer B prevents, from the inner surface of the casing 34, the impact from being transmitted to a battery 36, as in a case in which the gap G is formed. In addition, since the buffer B is provided between the battery 36 and a wall section 78, the vibration of the battery 36 caused by the impact to the casing 34 can be attenuated earlier than in the case in which the gap G is formed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A battery for a surgical instrument, comprising:
   a battery cell including:
      a substrate; and
      a first laminated body unit including a positive electrode layer, a solid electrolyte layer and a negative electrolyte layer, the positive electrolyte layer, the solid electrolyte layer and the negative electrode layer being laminated on a first side of the substrate, and the first laminated body unit being configured to generate electrical energy;

a casing including a storage to store the battery cell inside of the casing; and supports that are formed of an elastically deformable material and that are configured to support respective corners of the battery cell so as to maintain a state that the battery cell is spaced apart from an inner surface of the casing, wherein the supports comprise a first support, a second support, a third support, and a fourth support; the battery cell comprises a first corner, a second corner, a third corner, and a fourth corner; the first support being provided at the first corner, the second support being provided at the second corner, the third support being provided at the third corner, and the fourth support being provided at the fourth corner.

2. The battery according to claim 1, wherein the battery cell includes a second laminated body unit including a positive electrode layer, a solid electrolyte layer and a negative electrode layer, the positive electrode layer, the solid electrolyte layer and the negative electrode layer being laminated on a second side of the substrate which is opposite to the first side of the substrate, and the second laminated body unit being configured to generate electrical energy.

3. The battery according to claim 1, comprising a buffer between the inner surface of the casing and a surface of the first laminated body unit.

4. The battery according to claim 3, wherein the buffer has electrical insulating properties and heat resistance properties.

5. The battery according to claim 1, comprising contacts on the casing that is configured to transmit electrical energy.

6. The battery according to claim 1, wherein the solid electrolyte layer includes an inorganic solid electrolyte layer.

7. A surgical instrument unit comprising:
a surgical instrument including a housing with a grip adapted to be gripped by a hand of an operator; and
the battery of claim 1 attached to the housing.

8. The surgical instrument unit according to claim 7, wherein the casing is integrated with the housing of the surgical instrument.

9. The surgical instrument unit according to claim 7, comprising an end effector provided on the housing and configured to perform a treatment using the electrical energy of the first laminated body unit.

10. The surgical instrument unit according to claim 7, wherein each of the supports directly contacts the battery cell.

11. A surgical instrument comprising:
the battery of claim 1;
a housing attached to the battery; and
an end effector provided on the housing and configured to perform a treatment using the electrical energy of the first laminated body unit.

12. The surgical instrument according to claim 11, comprising a controller.

13. The surgical instrument according to claim 12, wherein the controller is configured to:
optimize charging of the battery cell at a time of charging; and
appropriately control the electrical energy when supplying energy to the end effector.

14. The surgical instrument according to claim 13, wherein the controller is configured to:
convert the energy into high frequency energy; and
supply the high frequency energy to the end effector.

15. The surgical instrument according to claim 13, wherein the controller is configured to:
control an energy converter and generate ultrasonic vibration with the energy converter by the energy; and
transmit the ultrasonic vibration to the end effector.

* * * * *